US012729187B2

(12) United States Patent
Ingram

(10) Patent No.: US 12,729,187 B2
(45) Date of Patent: Sep. 8, 2026

(54) OXIDATIVE PRETREATMENT OF CARBOHYDRATE DEHYDRATION PRODUCTS COMPRISING HUMINS

(71) Applicant: Archer Daniels Midland Company, Decatur, IL (US)

(72) Inventor: Andrew Ingram, Champaign, IL (US)

(73) Assignee: ARCHER-DANIELS-MIDLAND COMPANY, Decatur, IL (US)

(*) Notice: Subject to any disclaimer, the term of this patent is extended or adjusted under 35 U.S.C. 154(b) by 684 days.

(21) Appl. No.: 18/248,846

(22) PCT Filed: Oct. 11, 2021

(86) PCT No.: PCT/US2021/054451

§ 371 (c)(1),
(2) Date: Apr. 12, 2023

(87) PCT Pub. No.: WO2022/081495

PCT Pub. Date: Apr. 21, 2022

(65) Prior Publication Data

US 2023/0416215 A1 Dec. 28, 2023

Related U.S. Application Data

(60) Provisional application No. 63/090,836, filed on Oct. 13, 2020.

(51) Int. Cl.
*C07D 307/68* (2006.01)

(52) U.S. Cl.
CPC .................................. *C07D 307/68* (2013.01)

(58) Field of Classification Search
CPC ............................ C07D 307/68; C07D 307/46
USPC ......................................................... 549/485
See application file for complete search history.

(56) References Cited

U.S. PATENT DOCUMENTS

| | | | |
|---|---|---|---|
| 9,611,241 | B2 | 4/2017 | Boussie et al. |
| 10,017,486 | B2 | 7/2018 | Boussie et al. |
| 10,457,657 | B2 | 10/2019 | Metkar et al. |
| 10,538,499 | B2 | 1/2020 | Howard et al. |
| 2016/0207899 | A1 | 7/2016 | Yi et al. |
| 2019/0047973 | A1 | 2/2019 | Metkar et al. |

FOREIGN PATENT DOCUMENTS

| | | | | |
|---|---|---|---|---|
| CN | 107001306 | A | | 8/2017 |
| CN | 107739354 | A | | 2/2018 |
| CN | 107848995 | A | | 3/2018 |
| CN | 107848997 | A | | 3/2018 |
| CN | 109574962 | A | * | 4/2019 |
| EA | 037637 | B1 | | 4/2021 |
| GB | 621971 | A | | 4/1949 |
| JP | 2011506478 | A | | 3/2011 |
| JP | 2013231061 | A | | 11/2013 |
| JP | 2014528927 | A | | 10/2014 |
| JP | 2017505310 | A | | 2/2017 |
| RU | 2640203 | C2 | | 12/2017 |
| RU | 2732326 | C2 | | 9/2020 |
| RU | 2745266 | C2 | | 3/2021 |
| RU | 2750483 | C2 | | 6/2021 |
| WO | WO 2013-138153 | | | 9/2013 |
| WO | WO 2016-053186 | | | 4/2016 |
| WO | WO 2016-168233 | | | 10/2016 |
| WO | 2019072920 | A1 | | 4/2019 |
| WO | 2021123240 | A1 | | 6/2021 |

OTHER PUBLICATIONS

Mittal, N. et al., "One-pot synthesis of 2, 5-diformylfuran from fructose using a magnetic bi-functional catalyst", RSC advances, 2016, vol. 6. pp. 25678-25688 abstract; figure 9.

* cited by examiner

*Primary Examiner* — Taylor V Oh
(74) *Attorney, Agent, or Firm* — Andrew F. Nilles

(57) ABSTRACT

Processes for oxidative pretreatment of carbohydrate dehydration products are disclosed, which relate to the discovery that functional groups of humins, such as those that result in, or lead to, color formation (e.g., aldehyde groups and/or groups having conjugated double bonds) may be more readily converted by oxidation (in some cases "bleached") than FDCA-forming furanics. This selective oxidation of humins may use milder oxidation conditions and/or a different reaction system, compared to respective conditions and systems used for oxidation of furan ring-containing compounds. Oxidative pretreatment can beneficially promote the selective oxidation of humin functional groups over FDCA-forming furanics, with the overall result of modifying humins in a manner that can provide a number of improvements. These may particularly reside in the further processing of the obtained, pretreated dehydration product, such as in the overall manufacture of bio-based poly(alkylene furan dicarboxylate) copolymers, a prominent example of these being poly(ethylene furan dicarboxylate), or PEF.

18 Claims, No Drawings

OXIDATIVE PRETREATMENT OF CARBOHYDRATE DEHYDRATION PRODUCTS COMPRISING HUMINS

FIELD OF THE INVENTION

The present invention relates to processes for making the bio-based monomer, 2,5-furandicarboxylic acid (FDCA) from the oxidation of furanic species obtained from the dehydration of a hexose carbohydrate (e.g., fructose), and more particularly, to the processing of the crude dehydration product preliminary to this oxidation step to account for the presence of humins therein.

BACKGROUND OF THE INVENTION

The depletion of fossil fuels has created major incentives for seeking alternative sources to petroleum-based carbon for the synthesis of so-called "platform" molecules that can serve as the building blocks for commercially significant products. Biomass is currently viewed as a potential replacement from which many high value chemicals can be derived, but the development of sustainable technologies for the production of such chemicals from renewable resources remains a significant challenge.

The bio-based monomers, 2,5-furandicarboxylic acid (FDCA) and its dimethyl ester derivative, 2,5-furandicarboxylic acid, dimethyl ester (FDME) are recognized as important starting materials in the production of poly(alkylene furan dicarboxylate) polymers that can substitute for their known, mass-produced petroleum derived analogs, namely poly(alkylene terephthalate) polymers, such as polyethylene terephthalate (PET). A prominent example of a poly(alkylene furan dicarboxylate) polymer is poly(ethylene furan dicarboxylate), or PEF, obtained by reaction of FDCA or FDME with ethylene glycol. The bio-based polymer (bio-plastic) PEF exhibits superior properties in a number of respects, relative to its petroleum derived analog PET, particularly in the area of packaging. For example, blends of PEF and PET can provide improved barrier properties with respect to $CO_2$ and $O_2$, prolonging shelf life over that obtained with pure PET and providing an acceptable container for products such as beer that are susceptible to oxidative degradation. Other packaging applications of PEF include films used to manufacture pouches, wrappers, and heat shrink materials having high mechanical strength and recyclability.

In general, both FDCA and FDME are useful platform molecules in the production of polyamides, polyurethanes, and polyesters having diverse applications as plastics, fibers, coatings, adhesives, personal care products, and lubricants. The commercial significance of these molecules is evidenced, for example, in a 2004 study by the U.S. Department of Energy, identifying FDCA as one of twelve priority chemicals for establishing the "green" chemical industry of the future. Due to its structural similarity to terephthalic acid (TPA), the potential of FDCA as a substitute monomer for synthesizing polyesters has been recognized at least as early as 1946, for example in GB621971A, and a number of parties have invested significant effort over a number of years toward achieving a commercially viable process to manufacture FDCA. In terms of FDCA synthesis from bio-based starting materials, advancements are described in U.S. Pat. No. 10,538,499, according to which a feed comprising a six-carbon sugar unit (e.g., fructose) is subjected to integrated processing steps, the first of which is a dehydrating step to provide 5-hydroxymethylfurfural (HMF) or certain derivatives, such as its ester or ether derivatives. The dehydration product is then oxidized to the desired FDCA, according to a similar Mid-Century type oxidation as employed for the oxidation of p-xylene to make TPA, using a homogeneous catalyst system including cobalt, manganese and bromine components. Despite extensive development of these processing steps for manufacturing bio-based monomers, the commercial production of FDCA has not yet been realized. Improvements in proposed synthesis routes to FDCA remain a necessity for establishing economic viability on the commercial scale.

SUMMARY

Aspects of the invention relate to the discovery of methods for ameliorating or even eliminating detrimental effects associated with the presence of humins, which are highly colored and generally water-insoluble byproducts of the dehydration of carbohydrates, in processes utilizing such carbohydrates as starting materials in the bio-based synthesis of FDCA and derivatives thereof. The highly colored character of these byproducts is an evident detriment, given intended uses of the FDCA and derivatives to be prepared from a dehydration product including these humins in which an absence of color is desirable, for example, in the use of the FDCA and/or of its derivatives as a monomer for making polyester alternatives to PET for carbonated beverage bottles.

However, humins contained in dehydration products of carbohydrates having a six-carbon sugar unit (e.g., hexose sugars and their oligomers and polymers) also detrimentally tend to consume, or limit the useful capacity of, homogeneous Mid-Century oxidation catalysts. These are the catalysts that have been most proposed and most thoroughly evaluated for oxidizing 5-hydroxymethylfurfural (HMF) and/or its derivatives (e.g., ester and/or ether derivatives) that are formed in the upstream dehydration. It has been determined in this regard that, when byproduct humins are present in the oxidation feed together with HMF and/or its derivatives, operating parameters can become constrained. In a homogeneous catalyzed oxidation, this may manifest in (i) the need for increased catalyst concentration to maintain desired conversion and yield profiles, and/or (ii) a narrower "operating window" or set of conditions (temperature, pressure, time on stream) under which favorable performance is achieved, prior to loss of reaction or oxidation "light off" (e.g., based on a determination of oxygen consumption over the course of a reaction). Unfortunately, in the heterogeneous catalyzed processes that have been proposed for oxidizing HMF and/or its derivatives to provide FDCA, humins have also been determined to be problematic, in that they lead to catalyst deactivation as a result of their deposition on the solid catalyst particles. In both homogeneous and heterogeneous catalytic oxidation steps, therefore, increased catalyst consumption, which negatively impacts overall process economics due to expenses associated with higher amounts of catalyst feed, recovery, and recycle, can be attributed to the presence of humins.

In the face of these and other disadvantages associated with the oxidation of carbohydrate dehydration products having byproduct humins, it has now been discovered that a mild oxidative pretreatment to modify these humins is particularly advantageous. In general, oxidative pretreatment may be carried out under reaction conditions that are milder, relative to those known for the oxidation of the desired FDCA-forming furanics from carbohydrate dehydration (e.g., and especially HMF and its ester or ether derivatives) to FDCA. For example, oxidative pretreatment may utilize lower temperatures. Oxidative pretreatment may alternatively, or in combination, be characterized in that the desired FDCA-forming furanics are largely preserved across this step, e.g., the yield of these compounds is relatively unchanged, or is at least not significantly diminished. For example, the oxidation of FDCA-forming furanics such as HMF, or the esters or ethers of HMF, to FDCA by oxidative pretreatment may be minimal, or at least may be comparatively much less than that occurring in a downstream, or subsequent, oxidation. Alternatively, or in combination, oxidative pretreatment may be characterized by the use of an oxidizing agent that is not used in a downstream, or subsequent, oxidation, and/or by the use of a catalyst that is not used in a downstream, or subsequent, oxidation. Otherwise, rather than the use of a different oxidizing agent and/or catalyst, oxidative pretreatment may be characterized by the use of a different amount or concentration of an oxidizing agent and/or catalyst, relative to that used in a downstream, or subsequent, oxidation. Generally, oxidative pretreatment may be carried out under oxidative pretreatment conditions that differ in one or more respects (e.g., temperature, residence time, concentrations of one or more oxidizing agents and/or catalysts, and/or the use of one or more oxidizing agents and/or catalysts) relative to oxidation conditions for converting a comparably greater percentage of the desired, non-oligomeric and non-polymerized FDCA-forming furanics (such as HMF) to FDCA.

Regardless of the particular manner in which oxidative pretreatment may be distinguished or demarcated from the oxidation of such FDCA-forming furanics to FDCA, embodiments described herein relate to the important finding that functional groups of humins, such as those that result in, or lead to, color formation (e.g., aldehyde groups and/or groups having conjugated double bonds) may be more readily converted by oxidation (in some cases "bleached"), under certain oxidative pretreatment conditions, than HMF, HMF esters or HMF ethers, in particular. This selective oxidation of humins may use milder oxidation conditions and/or a different reaction system, compared to those/that used for oxidation of the desired, non-oligomeric and non-polymerized furanic precursors of FDCA that has been the focus of prior research efforts. Oxidative pretreatment can beneficially promote the selective oxidation of humin functional groups, with the overall result of modifying humins in a manner that can provide a number of improvements, particularly with respect to further processing of the obtained, pretreated dehydration product.

That is, an oxidative pretreatment step as described herein may be considered to cause the "selective" oxidation of humins, while substantially preserving intact the desired, non-oligomerized and non-polymerized FDCA-forming furanics such as HMF, its esters or ethers, for a subsequent oxidation directed to their conversion to FDCA, in the presence of humins having been beneficially modified in this oxidative pretreatment step. Modification of humins in a pretreated dehydration product, having been subjected to an oxidative pretreatment step, can result in a number of improved properties. These may include superior color, due to humin "bleaching," which can be measured by a reduction in absorption of ultraviolet or visible radiation by the pretreated dehydration product. Other improved properties of the pretreated dehydration product may include, or extend to, color reduction and/or improved color stability in downstream processing steps (e.g., oxidation, esterification and/or transesterification, and/or copolymer forming steps). Further improved properties may include, alternatively or in combination, (i) a decrease in average molecular weight of humins in the pretreated dehydration product, (ii) an increase in the quantity of precipitated humins in (facilitating the separation of humins from) this product, and/or (iii) an increase in the "processability," "oxidation robustness," or performance of this product in a downstream oxidation step, in terms of providing a more stable operation.

The content (e.g., percentage by weight) of dissolved and/or solid humins in a given dehydration product may be used as a basis for adjusting an operating condition of an oxidative pretreatment, such as increasing the severity of this pretreatment in the case of the humin content being increased. For example, the amount of an oxidizing agent added or fed to the oxidative pretreatment, relative to the amount of dehydration product (or the amount of FDCA-forming furanics in this product) added or fed to this pretreatment, may be increased upon the determination of an increased content of dissolved and/or solid humins (e.g., in the case of a continuous pretreatment). Otherwise, the amount of oxidizing agent present in an oxidative pretreatment (e.g., in an oxidative pretreatment vessel or reactor), relative to the amount of dehydration product (or the amount of FDCA-forming furanics in this product) present in this pretreatment, may be increased upon the determination of an increased content of dissolved and/or solid humins (e.g., in the case of a batch pretreatment). In other embodiments, a dry solids content of a dehydration feed, corresponding to the percentage by weight of hexose carbohydrates used in this feed, may be used in the same manner as using the content of dissolved and/or solid humins, as a basis for adjusting an operating condition of an oxidative pretreatment. This dry solids content typically bears a correlation to the content of dissolved and/or solid humins in the resulting dehydration product, in addition to the average molecular weight of these humins. That is, an increase in dry solids content can lead to an increase in both humin content and humin average molecular weight.

These and other aspects, embodiments, and associated advantages will become apparent from the following Detailed Description.

DETAILED DESCRIPTION OF EMBODIMENTS

The terms "wt-%" and "wt-ppm," as used herein, are used to designated percentage by weight and parts per million by weight, respectively. The term "mol-%" is used to designate a molar percentage.

Processes are described herein for making 2,5-furandicarboxylic acid (FDCA), using both an oxidative pretreatment step and an oxidation step. From the present disclosure, it can be appreciated that (i) oxidative pretreatment and (ii) an oxidation that results in a greater extent of conversion of FDCA-forming furanics to FDCA, may be performed in separate vessels or reactors, such as in the case of (i) being carried out in an oxidative pretreatment vessel or reactor and (ii) being carried out in a separate oxidation vessel or reactor, with operation of the oxidative pretreatment vessel or reactor utilizing oxidative pretreatment conditions as described herein. For example, all or a portion of the reaction product obtained from an oxidative pretreatment vessel or reactor may be conveyed to a downstream oxidation vessel or reactor, such as in the operation of a continuous process. Otherwise (i) and (ii) may be performed in separate zones within a single vessel or reactor, such as in the case of (i) being carried out in an oxidative pretreatment zone and (ii) being carried out in an oxidation zone, within the same vessel or reactor, with operation of the oxidative pretreatment zone utilizing oxidative pretreatment conditions as described herein. For example, the reaction product obtained from an oxidative pretreatment zone may be conveyed to a downstream oxidation zone, such as in the operation of a continuous process. Otherwise (i) and (ii) may be performed in the same vessel or reactor, such as in the case of (i) being carried out by subjecting a dehydration product to oxidative pretreatment conditions as described herein for a first, initial time period effective to provide a pretreated dehydration product, and (ii) being carried out by subjecting the pretreated dehydration product to different, oxidation conditions as described herein for a second, subsequent time period effective to provide a composition comprising FDCA (e.g., resulting from a greater extent of conversion of FDCA-forming furanics to FDCA under the oxidation conditions, compared to the extent of such conversion occurring under the oxidative pretreatment conditions). Performing (i) and (ii) in the same vessel or reactor may be characteristic of a batch process.

Processes described herein may include any of a number of further processing steps, while nonetheless benefitting from certain advantages associated with the oxidative pretreatment step as described herein. Such further processing steps may include a step of "esterifying" to form one or more ester derivatives of FDCA, whereby one or preferably both of the carboxylic acid groups of this dicarboxylic acid are converted to ester groups, such as alkyl ester groups (in the case of a mono- or dialkyl ester derivative) or aryl ester groups (in the case of a mono- or diaryl ester derivative), with methyl ester groups, ethyl ester groups, or phenyl ester groups being specific examples. In the case of methyl ester groups, the preferred ester derivative of FDCA is 2,5-furandicarboxylic acid, dimethyl ester (FDME), which can be formed by reaction of FDCA with a sufficient quantity of methanol.

Those skilled in the art having knowledge of the present disclosure will appreciate that processes described herein, including an oxidative pretreatment step, may also be applied in the production of a broad range of other derivatives of FDCA or indeed in the production of other oxidation products (other than FDCA) from an oxidation of the dehydration products from carbohydrates and/or in the production of desirable derivatives of these other oxidation products, including, but not limited to, ester derivatives; as well as hydroxyl (alcohol) derivatives, which include hydroxyalkyl derivatives; ether derivatives, which include alkoxy derivatives; amino derivatives; acyl derivatives, which include acyl halide derivatives such as acyl chloride derivatives; isocyanate derivatives; aldehyde derivatives; and acetal derivatives, where the unmodified humins would present similar difficulties as in the oxidation to make FDCA. As an example of such other oxidation products wherein the oxidative pretreatment step may be relevant, the dialdehyde diformyl furan (which can be made by the oxidation of species produced in the dehydration of fructose) may be more readily and easily converted into a diamino derivative than would FDCA. In the case of such derivatives, and more particularly for illustration purposes in the case of FDCA, one or both of the two carboxy-substituted furan ring members may instead be substituted with carboxylic acid groups other than carboxy and/or with other groups, to provide, for example, the corresponding diol, dialkanol (e.g., dimethanol), diamino, diacyl (e.g., diacyl chloride), diester, diisocyanate, ether-acid, ether-ester, ester-acid, ester-aldehyde, ether-aldehyde, ether-acetal, ester-acetal, acetal-acid, hydroxyl-acid, hydroxyalkyl-acid, hydroxyl-ester, hydroxyalkyl-ester, hydroxyl-acetal, hydroxyalkyl-acetal, hydroxyalkyl-hydroxyalkyl, diacetal and/or aldehyde-acetal derivatives, with the "acid" substitution referring to carboxy or a radical such as carboxymethyl, formed by a carboxylic acid other than acetic acid.

Yet further processing steps, beyond the formation of ester and other derivatives of FDCA and extending to the production of bio-based copolymers (e.g., copolyesters and others) are also described herein.

Dehydration Products and Humins Present in these Products

Particular embodiments are directed to processes for pretreating a dehydration product of one or more carbohydrates having a 6-carbon sugar unit (e.g., fructose), and in particular embodiments, a dehydration product that has not been refined to remove humins therefrom (a "crude" dehydration product). That is, the dehydration product is obtained from the dehydration of such one or more carbohydrates. A carbohydrate having a six-carbon sugar unit means a six-carbon sugar, an oligomer of a six-carbon sugar, or a polymer of a six-carbon sugar. Such carbohydrates include starch, amylose, galactose, cellulose, hemicellulose, inulin, fructan, glucose, fructose, sucrose, maltose, cellobiose, lactose, and sugar oligomers. These carbohydrates may also be referred to as hexose carbohydrates and may be obtained from one or a combination of products, byproducts, or intermediate products of wet or dry grain milling or cellulose/hemicellulose hydrolysis processes, with such products including one or more of fructose syrup, crystalline fructose, high fructose corn syrup, crude fructose, purified fructose, or molasses. A preferred carbohydrate is fructose, which may be provided to the dehydration step in pure or purified form (e.g., at greater than 90% or 95% purity).

As described above, the step of dehydrating will generally cause the formation, in the dehydration product comprising FDCA-forming furanics, of humins as byproducts. Humins refer to highly colored, generally brown to black, amorphous or non-crystalline polymers resulting from the dehydration of sugars. The concentration of humins in the dehydration product will depend at least partly on conditions, and particularly reaction severity, used in the dehydrating step, such that this concentration may correlate with the per-pass conversion. The concentration of humins and their relative molecular weight in a given sample may be determined by analytical methods such as gel permeation chromatography using a refractive index detector (GPC-RID). Humins are very generally considered detrimental to the downstream oxidizing of FDCA-forming furanics, as well as undesirable in terms of their ability to result in coloration of the bio-based polymer end product, yet at the same time must be seen as representing some of the intrinsic potential of hexose sugars for generating FDCA and its derivatives or other, value-added products that would ideally not be lost in the form of waste.

Consequently, representative processes may further comprise a step of separating at least a portion (e.g., an insoluble or precipitated portion) of the humins from the dehydration product, prior to the oxidative pretreatment (e.g., to provide an oxidation pretreatment feed having a reduced concentration of humins relative to the dehydration product). Alternatively, or in combination, to the extent that humins may be rendered insoluble by oxidative pretreatment, representative processes may further comprise a step of separating at least a portion (e.g., an insoluble or precipitated portion, such as that portion rendered insoluble or precipitated by oxidative pretreatment) of the humins from the pretreated dehydration product, following oxidative pretreatment. If removal of at least some portion of the humins is desired prior to the oxidizing of a dehydration product containing FDCA-forming furanics, the dehydration product or the pretreated dehydration product may be subjected to filtration, such as using an ultrafiltration (UF) membrane, taking advantage of the fact that at least a portion of the humins may be insoluble in aqueous media. Other methods for removing humins from the dehydration product or pretreated dehydration product, or from other intermediate products in the overall synthesis of bio-based polymers, include distillation and sublimation. Particular methods for humin removal are described, for example, in U.S. Pat. Nos. 10,457,657; 10,017,486; and 9,611,241, which patent publications are incorporated by reference for the disclosure of such methods.

However, certain aspects of the present disclosure relate to advantageous effects described herein that are achieved by oxidative pretreatment to modify humins, such as a reaction stabilizing effect of using the pretreated dehydration product in a subsequent oxidation to obtain a monomer composition comprising FDCA. These effects may obviate the need for supplemental steps to remove humins (assuming there are not alternative higher value options to upgrade or use directly some portion of the humins, which provide an independent reason for removal) and therefore, according to some embodiments, the dehydration product is not processed (e.g., filtered) to remove humins, or the pretreated dehydration product is not processed (e.g., filtered) to remove humins, or neither of these products is processed to remove humins.

Oxidative Pretreatment of Dehydration Products

Representative processes comprise, in an oxidative pretreatment step, contacting the dehydration product with an oxidizing agent to provide a pretreated dehydration product having (e.g., relative to the dehydration product) an improved property resulting from modifying humins present in the dehydration product. Such modifying may, for example, selectively convert aldehyde-containing functional groups of humins present in the dehydration product (e.g., formed in the upstream dehydration of the one or more carbohydrates) and thereby eliminate their tendency to otherwise undergo aldol condensation and produce color over time in the pretreated dehydration product and/or downstream products such as a composition comprising FDCA that is provided following a subsequent oxidation of the pretreated dehydration product. In the oxidative pretreatment step, FDCA-forming furanics present in the dehydration product may be largely preserved (remain unconverted) in the pretreated dehydration product, such that the oxidative pretreatment step may be characterized by a selective modification of humins, without substantial conversion, such as by oxidation, of these FDCA-forming furanics. For example, in representative embodiments, the yield of FDCA-forming furanics in the pretreated dehydration product is at least about 80 mol-%, i.e., the moles of FDCA-forming furanics recovered in the pretreated dehydration product represent at least about 80% of those present in the dehydration product, prior to oxidative pretreatment. In other embodiments, the yield of FDCA-forming furanics, obtained from oxidative pretreatment, is at least about mol-%, at least about 90 mol-%, or at least about 95 mol-%.

Likewise, according to some embodiments, the weight percentage of humins present in the dehydration product may also be largely preserved, although these humins may be substantially modified by oxidative pretreatment, such that an improved (lighter) color of the pretreated dehydration product may be perceived visually and/or may be measured quantitatively, as described herein. For example, in representative embodiments, the yield of humins in the pretreated dehydration product is at least about wt-%, i.e., the weight of humins recovered in the pretreated dehydration product represents at least about 85% of that present in the dehydration product, prior to oxidative pretreatment. In other embodiments, the yield of humins, obtained from oxidative pretreatment, is at least about 90 mol-%, at least about 95 mol-%, or at least about 97 mol-%.

FDCA-forming furanics refer to furan ring-containing monomeric and dimeric molecules that form FDCA through catalytic oxidation, in an oxidation step as described herein. FDCA-forming furanics may be obtained along with humins in a dehydration product, from dehydrating one or more carbohydrates having a six-carbon sugar unit at elevated temperatures and in the presence of an acid catalyst, which may be homogeneous or heterogeneous in nature. FDCA-forming furanics include 5-(hydroxymethyl)furfural (HMF), and, in the case of their formation in the presence of a lower carboxylic acid such as acetic acid, can include ester derivatives of HMF, such as 5-(acetoxymethyl)furfural, or, in the case of their formation in the presence of a lower alcohol solvent (e.g., methanol), can include ether derivatives of HMF, such as 5-(methoxymethyl)furfural. Other FDCA-forming furanics can include derivatives of HMF such as 2,5-diformylfuran and 5-formyl-2-furancarboxylic acid. FDCA-forming furanics further include the HMF dimer 5,5'-[oxybis(methylene)]di(2-furaldehyde), as well as HMF oligomers. Examples of non-FDCA forming furanics include, but are not limited to, furfural, 2-(hydroxyacetyl) furan, and 2-(acetoxyacetyl)furan. In preferred embodiments, the dehydration product, as well as the pretreated dehydration product, may comprise, such that the FDCA-forming furanics may include, one or more of HMF and/or an ester or ether derivative thereof. In the case of the dehydration being performed using an acetic acid catalyst and solvent, the FDCA-forming furanics may include, or may consist essentially of, HMF, 5-(acetoxymethyl)furfural, and HMF dimer.

In one embodiment, the dehydration may utilize hydrobromic acid in addition to acetic acid and may be integrated, such as through an intermediate oxidative pretreatment as described herein, with a subsequent Mid-Century type oxidation step such that the dehydration product is fed directly into the subsequent oxidative pretreatment step, and the pretreated dehydration product obtained from this step is fed, in turn, to an oxidation step, for example according to an oxidation step as described in U.S. Pat. No. 10,538,499. The integration of dehydrating (or dehydration) and oxidizing (or oxidation) steps, such as through an intermediate oxidative pretreatment step, may provide advantages including those arising from the use of the same acetic acid (or acetic acid and water) solvent in two or all three of these steps. Furthermore, the use of a common solvent, in addition to the suitability of hydrobromic acid for use as a further acid catalyst for the dehydration step, provides the added advantage that acetic acid and optionally at least a portion of the bromine source for the Mid-Century oxidation step (in the form of hydrobromic acid, typically), can be recycled (and preferably substantially completely recycled) from the oxidizing step back to the dehydrating step. These components, namely hydrobromic acid and acetic acid, can likewise be utilized in the intermediate oxidative pretreatment step, in a similar manner as in the oxidation step. This results in significant capital and operating cost reduction associated with converting a carbohydrate having a six-carbon sugar unit to FDCA.

In general, following the oxidative pretreatment, the pretreated dehydration product may be subjected to an oxidation step, in an overall process for making a monomer composition comprising FDCA. The process may comprise contacting all or a portion of the pretreated dehydration product (e.g., as an oxidation feed), in the presence of oxygen (e.g., an oxygen-containing gas such as air), with an oxidation catalyst to provide the composition comprising FDCA. In the oxidation step, FDCA-forming furanics present in the pretreated dehydration product may be largely converted (oxidized) in the composition comprising FDCA. For example, in representative embodiments, the yield of FDCA in the oxidation step, based on FDCA-forming furanics in the pretreated dehydration product, may be at least about 60 mol-%, i.e., the moles of FDCA recovered in the composition comprising FDCA may represent at least about 60% of the moles of FDCA-forming furanics in the pretreated dehydration product. In other embodiments, the yield of FDCA, obtained from oxidation, is at least about 70 mol-%, at least about 80 mol-%, or at least about 90 mol-%. For example, the moles of FDCA-forming furanics remaining in the composition comprising FDCA may represent less than about 40%, less than about 30%, less than about 20%, or less than about 10%, of those present in the oxidation feed, or pretreated dehydration product, prior to oxidation. The oxidation step may comprise, more particularly, feeding all or a portion of the pretreated dehydration product, as an oxidation feed, to an oxidation reactor containing an oxidation catalyst (e.g., a homogeneous or heterogeneous catalyst) and reactant oxygen.

In the oxidative pretreatment, the contacting of the dehydration product with an oxidizing agent may be performed, for example, by continuously adding these oxidative pretreatment feeds to a vessel or reactor in desired amounts, such as in a given ratio of oxidizing equivalents provided by the oxidizing agent, relative to moles of FDCA-forming furanics provided by the dehydration product. The contacting may also be performed, more generally, if the oxidizing agent and dehydration product are present together in a vessel or reactor in such desired amounts. Whether the oxidative pretreatment feeds are continuously added to a vessel or reactor, such as in the case of a continuous operation, and/or these feeds are present together in a vessel or reactor, such as in initial desired amounts (a given molar ratio as described above) that are charged to the vessel or reactor in the case of a batch operation, the contacting between the dehydration product and oxidizing agent occurs under appropriate oxidative pretreatment conditions effective to achieve a selective modification of humins present in the dehydration product. In this manner, the resulting, pretreated dehydration product may have, relative to the dehydration product, an improved property resulting from modifying humins initially present in this product, without substantial conversion of FDCA-forming furanics in this product.

Improved properties, which may result from the selective conversion of aldehyde-containing functional groups of humins present in the dehydration product, or which may result from other transformations occurring in the oxidative pretreatment, can include an improved color of the pretreated dehydration product, which may be determined qualitatively (e.g., through observation) or quantitatively, such as by a reduction in an absorption of ultraviolet or visible radiation. For example, according to a specific embodiment, the pretreated dehydration product may exhibit a reduction in the absorption of light, as determined at a particular wavelength, such as 460 nanometers (nm). The absorption may be, for example, about 80% or less, relative to that of the untreated dehydration product, i.e., the absorption may be reduced by at least about 20%. In other embodiments, the absorption may be about 70% or less, about 60% or less, or about 50% or less, relative to that of the dehydration product. Other improved properties may include, alternatively or in combination, the ability to further process the pretreated dehydration product with a reduced color formation and/or increased color stability in downstream processing steps and in resulting downstream products (e.g., FDCA, esterified derivatives of FDCA, prepolymers that are reaction products of FDCA or esterified derivatives of FDCA with a co-monomer, and copolymers formed from polycondensation of such prepolymers). Yet other improved properties may include, alternatively or in combination, a decrease in the average molecular weight of humins in the pretreated dehydration product, relative to that of humins in the dehydration product prior to oxidative pretreatment. The decrease in molecular weight may result, for example, from cleaving of humins by reaction with an oxidizing agent. Still other improved properties may include, alternatively or in combination, an increase in the quantity (e.g., percentage by weight) of precipitated (solid) humins present in the pretreated dehydration product, relative to that present (e.g., as suspended solids) in the dehydration product prior to oxidative pretreatment. In this case, representative processes may comprise a step of removing solid humins from the pretreated dehydration product, such as by filtration, prior to further processing, such as by oxidizing FDCA-forming furanics in this product to FDCA. Still other improved properties may include, alternatively or in combination, an increase in stability of the pretreated dehydration product, as a feed for this oxidation, i.e., as an oxidation feed for producing FDCA. That is, relative to an otherwise comparable but untreated dehydration product, the pretreated dehydration product may provide improved performance with respect to any, or any combination, of operating parameters described herein (e.g., those parameters described above) as being constrained in homogeneous or heterogeneous catalyzed oxidation, due to the presence of humins. For example, the pretreated dehydration product may require a reduced catalyst consumption, relative to the untreated dehydration product, in a given oxidation step.

Representative oxidizing agents that may be utilized in the oxidative pretreatment include oxygenated compounds, such as those in which one or more oxygen atoms has an oxidation state of −1 or less, for example in the case of peroxy compounds. Specific types of suitable oxidizing agents include transition metal oxides (e.g., manganese oxide), alkali or alkaline earth metal oxyhalides (e.g., sodium oxychloride), alkali or alkaline earth metal percarbonates (e.g., sodium percarbonate), alkali or alkaline earth metal permanganates (e.g., potassium permanganate), alkali or alkaline earth metal chlorates or perchlorates (e.g., potassium perchlorate), alkali or alkaline earth metal bromates or perbromates (e.g., potassium bromate), alkali or alkaline earth metal iodates or periodates (e.g., sodium periodate), alkali or alkaline earth metal sulfates or persulfates (e.g., potassium hydrogen monopersulfate, or Oxone®), peroxides (e.g., hydrogen peroxide), a peroxy acid (e.g., peracetic acid or meta-chloroperoxybenzoic acid), or oxygen (e.g., contained in air). Combinations of these types and/or specific compounds may be used as oxidizing agents. In one embodiment, therefore, the oxidizing agent may be selected from one or more of $MnO_2$, NaOCl, $H_2O_2$, $KHSO_5$ (Oxone®), $Na_2CO_3 \cdot 1.5H_2O_2$, meta-chloroperoxybenzoic acid, peracetic acid, $KMnO_4$, $NaIO_4$, and $KBrO_3$. In the case of alkali or alkaline earth metal bromates or perbromates, the oxidizing agent may be a bromine source that yields $Br_2$ and that contributes to the selective oxidation, such as the selective "bleaching," of humins. A bromine source may be used alone, such as in the case of using an alkali or alkaline earth metal bromate or perbromate alone; multiple bromine sources may be used; or one or more bromine sources may be used in combination with one or more non-bromine containing oxidizing agents, such as those described above (e.g., $MnO_2$). Bromine sources include those described herein with respect to their use in the dehydrating step (e.g., hydrobromic acid) and also include bromine-containing species as described herein with respect to their use in an oxidation step. In preferred embodiments, any of the oxidizing agents or combinations of oxidizing agents, as described herein, may be solubilized in the dehydration product, or in a reaction mixture comprising this product, during oxidative pretreatment. However, certain oxidizing agents having limited aqueous solubility may otherwise be used in solid form, such as in the form of fine solid particulates that may be separated following the oxidative pretreatment and prior to further processing of the pretreated dehydration product, for example, using filtration.

The oxidative pretreatment may be performed by initially charging, or continuously adding, an oxidizing agent as described herein to a vessel or reactor, to which the dehydration product is also charged and/or continuously added. Beneficially, the oxidizing agent may be used in a relatively minor amount, such as in a sub-stoichiometric amount with respect to FDCA-forming furanics (e.g., with respect to the number of moles of HMF, 5-(acetoxymethyl)furfural, and HMF dimer) in the dehydration product. In some embodiments, the oxidizing agent may be present (in a suitable vessel or reactor) or may be added (to a suitable vessel or reactor) in an amount representing less than about 85 mol-% (e.g., from about 5 mol-% to about 85 mol-%) of oxidizing equivalents, relative to the FDCA-forming furanics. Oxidizing equivalents are based on the number of atoms in a given oxidizing agent having oxidizing capability (e.g., oxidizing oxygen atoms and oxidizing halogen atoms), such that, for example, 1 mole of NaOCl represents 2 moles of oxidizing equivalents. In other embodiments, the oxidizing agent may be present, or added, in an amount representing less than about 70 mol-% (e.g., from about 5 mol-% to about 70 mol-%) of oxidizing equivalents. For example, the oxidizing agent may be present, or added, in an amount representing from about 10 mol-% to about 70 mol-%, from about 10 mol-% to about 50 mol-%, from about 25 mol-% to about 70 mol-%, from about 35 mol-% to about 70 mol-%, or from about 25 mol-% to about 50 mol-%, of oxidizing equivalents. In general, with all other parameters being equal, an increased dry solids content of a dehydration feed, corresponding to the percentage by weight of hexose carbohydrates used in this feed and correlating to an increased content of dissolved and/or solid humins in the dehydration product, will warrant the use of an increased amount of oxidizing agent(s), in terms of oxidizing equivalents present or added.

In the case of co-feeding (i) a dehydration product comprising FDCA-forming furanics and (ii) an oxidizing agent to a vessel or reactor used to perform oxidative pretreatment, these feeds (i) and (ii) may be provided as separate streams (e.g., input at separate locations) to the same vessel or reactor. For example, the separate streams may enable a more desirable temperature profile within the vessel or reactor, or otherwise provide improved control over this temperature profile, such as by positioning or manipulating the exothermic heat release. Alternatively, the feeds (i) and (ii) may be provided as a combined feed stream to the vessel or reactor, such as in the case of combining a stream of the oxidizing agent with the effluent of a dehydration reactor comprising the dehydration product. In still further embodiments, portions of the feeds (i) and (ii) may be combined upstream of the vessel or reactor and/or added as separate streams, depending on objectives relating to process efficiency and process control. In the case of a batch operation, the co-feeding of (i) and (ii) may involve initially charging these feeds, for example in relative amounts described above, to the vessel or reactor and performing the oxidative pretreatment for a time and at a temperature that will be effective for modifying the humin content of the resulting dehydration product as described herein.

Whether the oxidative pretreatment is performed continuously or batchwise, the dehydration product and oxidizing agent may be contacted in the presence of a catalyst and/or other components as described herein as also being generally suitable for use in oxidation of the pretreated dehydration product to provide a composition comprising FDCA, from the oxidation of FDCA-forming furanics in the dehydration product, or, more particularly, from the oxidation of at least a portion of these FDCA-forming furanics, which remains in the pretreated dehydration product. Exemplary catalysts comprise one or more metals from Groups 5-11 of the periodic table (IUPAC version), for example soluble forms of any of these metals, with more particular catalysts comprising soluble forms of Co and/or Mn. Any of these metals may be present, for example in a reaction mixture used to carry out oxidative pretreatment and comprising the dehydration product and any oxidizing agent(s) described herein, independently in an amount, or otherwise in a combined amount, representing from about 0.1 mol-% to about 10 mol-%, such as from about 1 mol-% to about 5 mol-%, of FDCA-forming furanics in the dehydration product that is present in such reaction mixture. Alternatively, or in addition, the catalyst may comprise an acid, such as nitric acid ($HNO_3$), which may be present in the reaction mixture in an amount within these ranges or otherwise may be present, in a higher amount or a lower amount. For example, an acid may be present in an amount representing from about 0.05 mol-% to about 5 mol-%, such as from about 0.1 mol-% to about 1 mol-%, of FDCA-forming furanics in the dehydration product. An exemplary catalyst, or catalyst system, comprises soluble forms of Co and/or Mn, present in a reaction mixture, optionally together with an acid (e.g., $HNO_3$), with the metal and optional acid components having concentrations within these ranges based on FDCA-forming furanics.

In some embodiments, an oxidative pretreatment to primarily modify humins and a subsequent oxidation to primarily convert FDCA-forming furanics to FDCA may be carried out in the same vessel or reactor. However, whether or not the same vessel or reactor is used for these steps, oxidative pretreatment and oxidation may be differentiated, according to some embodiments, in that the former is carried out under milder conditions relative to the latter. For example, an oxidative pretreatment temperature used in the oxidative pretreatment may be lower than an oxidation temperature used in the oxidation step. A representative temperature, or average temperature, of a reaction mixture comprising the dehydration product and oxidizing agent and suitable for the oxidative pretreatment, may be from about room temperature (i.e., about 20° C.) to about 120° C. In other embodiments, the temperature, or average temperature, may be less than about 100° C. (e.g., from about 20° C. to about 100° C.), or less than about 80° C. (e.g., from about 20° C. to about 80° C.). Such temperature, or average temperature, may be used in conjunction with a suitable residence time, over which the dehydration product and oxidizing agent are maintained in contact (e.g., in a batch or continuous process), such as a residence time of at least 1 hour (e.g., from about 1 hour to about 24 hours, from about 1 hour to about 12 hours, or from about 1 hour to about 6 hours). For example, in the case of a batch process, the dehydration product and oxidizing agent may be (i) charged to a vessel or reactor, such as in relative amounts as described herein, (ii) subjected to an oxidative pretreatment step under conditions, including an average temperature for a given residence time, as described herein, and (iii) after this residence time, subjected to an oxidation step under more severe conditions, including a higher average temperature and/or other conditions as described herein as being generally suitable for use in oxidation of the pretreated dehydration product to provide a composition comprising FDCA.

Whether performed continuously or batchwise, oxidative pretreatment and oxidation may be carried out using the same catalyst or catalyst system, optionally with the same concentration(s) of catalyst(s) and/or same ratios with respect to FDCA-forming furanics in the respective feeds. In some embodiments, oxidative pretreatment and oxidation may be differentiated by the use of an oxidizing agent, as described herein, in the former that is not used in the latter. Whether or not these steps are differentiated in this manner, oxygen (e.g., contained in air) may be used as an oxidizing agent in both steps. As described above, the oxidative pretreatment, which may comprise co-feeding the dehydration product and oxidizing agent, may be further combined, in an integrated or non-integrated manner, with a further step prior to the co-feeding, of dehydrating one or more carbohydrates in a dehydration feed to obtain the FDCA-forming furanics. This dehydrating may be performed with the one or more carbohydrates (e.g., selected from hexose sugars) being in a solution comprising, as a solvent, a lower carboxylic acid (e.g., acetic acid) or a lower alcohol (e.g., methanol or ethanol).

Particular embodiments of the invention are directed to processing options, as well as overall processing flexibility, arising from the use of an oxidative pretreatment to partially or completely restore performance (e.g., catalyst activity) in the oxidation of FDCA-forming furanics to form FDCA, relative to a comparative (or baseline) oxidation performed in the absence of the oxidative pretreatment but having the humins removed from, or absent in, the dehydration product. Advantageously, performance restoration may be realized using only a minor amount of the oxidizing agent (e.g., on a molar basis) relative to the dehydration product, based on the portion thereof that is oxidizable to the desired monomer (e.g., "on path" FDCA-forming furanics). Representative processes for pretreating a dehydration product, or otherwise for making a monomer composition comprising FDCA, may comprise contacting a dehydration product of one or more carbohydrates having a 6-carbon sugar unit with an oxidizing agent as described herein, to provide a pretreated dehydration product, according to an oxidative pretreatment step. In such processes, an amount of the oxidizing agent that is added (e.g., in the case of continuous operation), or an amount of the oxidizing agent that is present (e.g., in the case of bath operation) may be adjusted based on the humin content of the dehydration product, or, as a proxy for this humin content, based on the dry solids content of the dehydration feed.

Dehydrating Carbohydrates for Making FDCA-Forming Furanics

Representative processes comprise, prior to an oxidative pretreatment step, a dehydrating step for making FDCA-forming furanics as described above, all or a portion of which are used (e.g., as a component of an oxidative pretreatment feed for, or as a stream for co-feeding to) in this oxidative pretreatment step. The dehydrating step may be performed batchwise, whereby the FDCA-forming furanics are recovered and intermittently transferred to the oxidative pretreatment step, but preferably the dehydrating step is performed continuously with continuous transfer. In any event, an upstream step of the process may therefore comprise dehydrating a dehydration feed comprising one or more carbohydrates having a six-carbon sugar unit, as described above. This dehydration feed (e.g., an aqueous fructose solution) may have a dry solids concentration from about 5 wt-% to about 50 wt-%, such as from about 10 wt-% to about 30 wt-% or from about 5 wt-% to about 35 wt-%, and/or may be prepared from a purified source of the six-carbon sugar, such as fructose having a purity of at least 90 wt-% (e.g., 97 wt-% fructose).

The dehydrating may occur in the presence of a Bronsted acid source (which can be or can include a bromine source such as HBr used and recycled in the context of an integrated dehydration-Mid Century-catalyzed oxidation sequence as described in U.S. Pat. No. 10,538,499) and a solvent for the FDCA-forming furanics, and may be performed at an elevated temperature and for a time sufficient to generate the oxidative pretreatment feed comprising FDCA-forming furanics, such as HMF and/or its derivatives. Depending on the solvent, the derivative(s) may include an ester derivative, an ether derivative, and/or HMF dimer. The oxidative pretreatment feed, comprising some or all of the product formed in the dehydrating step (dehydration product) as a component, will generally also comprise at least a portion of the solvent. That is, all or a portion of the solvent, such as a mixture of acetic acid and water, that is used in the dehydrating step, may be passed to the oxidative pretreatment step, in addition to all or a portion of any water generated in this step. The solvent may otherwise comprise an alcohol such as methanol, ethanol, or a higher alcohol, or possibly a cyclic or heterocyclic hydrocarbon compound (e.g., dioxane). Solvent is preferably separated following an oxidation step, subsequent to the oxidative pretreatment step, to provide, in addition to a monomer composition comprising FDCA as described herein, a solvent recycle stream back to the dehydrating step. This recycle stream will generally also contain the Bronsted acid source (e.g., HBr). The solvent recycle stream will generally further contain FDCA-forming furanics, such that the total amount of FDCA-forming furanics in the dehydration product may include a portion that has been newly generated in a pass through the dehydrating step (i.e., based on a "per-pass conversion") and a portion that has been recycled back from the downstream oxidation step.

Where a bromine source is used in the dehydrating step, that bromine source, as well as any bromine source that may be used in the oxidative pretreatment step as an oxidizing agent, can generally be any compound that provides bromide ions or radicals in the reaction mixture. Representative bromine sources for use in either step include hydrogen bromide, hydrobromic acid, sodium bromide, potassium bromide, molecular bromine, benzyl bromide, and tetrabromoethane. In the case of hydrogen bromide being used (for example, at least in part in the form of recycled hydrogen bromide in the context of an integrated process as described in U.S. Pat. No. 10,538,499, now incorporated herein by reference for the description of particular dehydration methods wherein a bromine source is employed), this compound, in the presence of the dehydration feed and solvent, may act as an acid catalyst in the dehydrating step, upon dissociation to form hydrobromic acid. In certain other embodiments, bromine sources such as 1-alkylpyridinium bromides and 1,3-dialkylimidazolium bromides may be useful as promoters in the presence of a solvent comprising acetic acid and water. Regardless of the particular bromine source, the step of dehydrating therefore provides a dehydration product, some or all of which may be used a component of the subsequent oxidative pretreatment step.

Oxidizing the Pretreated Dehydration Product, for Making a Monomer Composition

Representative methods comprise an oxidation step of contacting an oxidation feed, in the presence of oxygen, with an oxidation catalyst to provide a monomer composition comprising FDCA as described herein. The oxidation feed may comprise the pretreated dehydration product, as described herein, or at least a portion of this product, such as a portion obtained following the removal of humins as described above. The oxidation feed may further comprise all, or a portion of the solvent used initially to prepare the dehydration feed and/or at least one bromine-containing species. The oxygen may be obtained using, as a source, air, purified oxygen, or other oxygen-containing feed. The oxidizing step may be performed batchwise, but is preferably performed continuously, with at least the pretreated dehydration product (or portion thereof), oxygen-containing feed, and optionally catalyst, being fed continuously to an oxidation reactor, and the monomer composition being continuously withdrawn from this reactor.

Particular methods may comprise contacting the oxidation feed with a metal-containing catalyst and the oxygen-containing feed at an elevated temperature for a time sufficient to produce, as an oxidation product, a monomer composition comprising FDCA and/or its derivatives, solvent, and residual catalyst. As shown in US for example, some or substantially all of the bromine required for a Mid Century process-type oxidation may be provided by means of bromine-containing species (such as recycled HBr) in the oxidation feed prepared from the preceding dehydration step. Representative bromine-containing species include inorganic bromides such as HBr; metal bromides such as lithium bromide, sodium bromide, potassium bromide, magnesium bromide, calcium bromide, cobalt bromide, and manganese bromide; and organic bromides such as 5-(bromomethyl) furfural and derivatives thereof, and brominated furanic oligomers. A supplemental bromine source may be introduced to the oxidizing step (e.g., fed to the oxidation reactor), if necessary given the bromine content provided by bromine-containing species in the oxidation feed from the dehydrating step and/or the oxidative pretreatment step.

In the case of homogeneous (liquid phase) oxidation catalysts, metal-containing catalysts in particular can be effective for converting HMF and/or other FDCA-forming furanics (e.g., HMF esters and/or HMF ethers) in the oxidation feed (depending on the solvent used in the dehydrating step) to FDCA and/or its derivatives. These metal-containing catalysts may alternatively, or also, be utilized in oxidative pretreatment to modify humins in the dehydration product (e.g., under milder conditions compared to those used for oxidation to form monomers), as described herein. Representative metal-containing catalysts, for use in either or both of the oxidative pretreatment and/or oxidation steps, may comprise one or more transition metals, such as either or both of Co and Mn, optionally in combination with Zr, Ce, Zn, Mo, Bi, V, and/or Ni. The metal-containing catalyst may react with the bromine present in the bromine-containing species, as described above, to form metal bromides in situ. According to particular embodiments, the metal catalyst may be present in a reaction mixture that is contained in the oxidative pretreatment reactor or oxidation reactor (which may comprise the same vessel or different vessels, as described above), such that the concentrations of the one or more transition metals are independently in the range from about 5 wt-ppm to about 10,000 wt-ppm, such as from about 10 wt-ppm to about 8,000 wt-ppm or from about 50 wt-ppm to about 5,000 wt-ppm. For example, Co may be present in the reaction mixture in a concentration from about 10 wt-ppm to about 10,000 wt-ppm, from about 10 wt-ppm to about 8,000 wt-ppm, from about 59 wt-ppm to about 5,900 wt-ppm, or from about 2,000 to about 4,000 wt-ppm. Mn may be present in the reaction mixture in a concentration from about 5 wt-ppm to about 10,000 wt-ppm, from about 5 wt-ppm to about 8,000 wt-ppm, from about 55 wt-ppm to about 5,500 wt-ppm, or from about 200 to about 1,000 wt-ppm. Bromine, from the bromine-containing species and/or bromine source, may be present in the reaction mixture from about 0.1 wt-ppm to about 20,000 wt-ppm, from about 200 wt-ppm to about 20,000 wt-ppm, from about wt-ppm to about 10,000 wt-ppm, or from about 1,000 wt-ppm to about 2,000 wt-ppm.

Oxidizing conditions, or conditions maintained in the oxidizing reactor, which will generally differ in at least one respect compared to conditions used for oxidative pretreatment, even if the same reactor is used for both steps, may include a temperature from about 120° C. to about 250° C., such as from about 170° C. to about 190° C., and an oxygen partial pressure from about 0.02 bar to about 100 bar, from about 0.02 bar to about 21 bar, from about 0.2 bar to about 100 bar, or from about 0.2 bar to about 21 bar. The total absolute pressure in the oxidizing reactor may be from about 1 bar to about 200 bar, such as from about 5 bar to about 100 bar or from about 10 bar to about bar. Molar yields of monomers from the oxidizing step, such as the molar yield of FDCA on the basis of the FDCA-forming furanics in the oxidation feed, may be at least about 60%, at least about 70%, at least about 80%, at least about 90%, or at least about 95%. Following the oxidizing step, the resulting monomer(s) including FDCA may be separated from the oxidation reaction mixture, including the solvent, for further purification. At least a portion of the solvent, from which the monomer(s) is/are separated, may then be recycled back to the dehydration reactor, together with at least a portion of unconverted FDCA-forming furanics. Since FDCA is largely insoluble in solvents comprising acetic acid or mixtures of acetic acid and water under mild conditions, separation of FDCA in embodiments utilizing such solvents may be easily accomplished by filtration and/or centrifugation following precipitation from the oxidation reaction mixture. Particular methods for oxidizing to form monomers are described, for example, in U.S. Pat. No. 10,538,499, which is incorporated by reference for the disclosure of such methods.

Esterifying Monomers

Steps of esterifying monomers such as FDCA, for forming ester derivatives, comprise reacting these monomers with an esterifying agent such as an alcohol, for example methanol if a dimethyl ester is desired or ethanol if a diethyl ester is desired, or possibly phenol, if a diphenyl ester is desired. The reaction of FDCA or other monomer(s) with the appropriate alcohol, or phenol, may be carried out in an esterification reaction mixture including a high boiling point solvent (e.g., dimethyl sulfoxide, dimethylacetamide, sulfolane, FDME, γ-butyrolactone, isosorbide or its dimethyl ether, propylene carbonate, adipic acid, isophorone, ethyl phenyl ether, diphenyl ether, dibenzyl ether, aromatic 200 fluid, butyl phenyl ether, methyl heptyl ketone, ethyl phenyl ketone, 2'-hydroxyacetophenone, decahydronaphthalene, tetrahydronaphthalene, etc.) under suitable esterification conditions. These may include a temperature from about 30° C. (86° F.) to about 350° C. (662° F.) and a pressure from about atmospheric pressure to about 3.5 megapascal (MPa), and the esterification reaction may be performed together with distillation (according to a reactive distillation process) for separation of the FDME or other ester derivative.

In preferred embodiments, a step of esterifying the monomer composition, which contains FDCA that is obtained from oxidation, comprises reacting the monomer composition, or a separated fraction thereof (e.g., a fraction enriched in FDCA relative to the monomer composition as a whole, which is obtained directly from oxidation) with methanol as the esterifying agent. This may provide an esterified monomer composition comprising FDME, which may be a desirable ester derivative monomer due to its lower boiling point relative to the parent dicarboxylic acid, FDCA, rendering FDME amenable to separation by distillation.

Polymer Forming from a Monomer Composition Comprising FDCA or Esterified Derivative Monomer compositions comprising FDCA and/or its derivatives may be used for forming polymers, and particularly bio-based copolymers having FDCA-related moieties (e.g., furandicarboxylate moieties). In general, representative polymer forming steps can include, for the production of polyesters, (i) esterifying a monomer composition comprising FDCA or separated fraction thereof, as described herein, or (ii) transesterifying an esterified monomer composition (e.g., comprising FDME) or separated fraction thereof, as described herein, and, following either (i) or (ii), polymerizing by polycondensation. Representative polyester polymer forming steps involve the polymerization of monomers or ester derivative monomers described herein, such as the monomer FDCA or the ester derivative monomer FDME, with suitable co-monomers such as diols. For example, ethylene glycol may be used as the co-monomer to produce poly(ethylene furan dicarboxylate) (PEF) from FDCA or FDME. The co-monomer 1,3-propane diol may be used to produce poly(trimethylene furan dicarboxylate) (PTF) from FDCA or FDME.

Particular methods may comprise producing a precursor composition comprising a prepolymer that is an esterified intermediate such as the reaction product of FDCA with the co-monomer, or a transesterified intermediate such as the reaction product of FDME with the co-monomer. The prepolymer, whether an esterified intermediate or transesterified intermediate, is functionalized with terminal alcohol groups (e.g., rather than terminal carboxylate groups of FDCA or terminal methyl groups of FDME) and therefore may then be subjected to polycondensation to provide a copolymer as described herein, and particularly a poly (alkylene furan dicarboxylate) polymer. Processes for producing a polyester polymer (e.g., copolyester) can therefore include both a first, esterification or transesterification step to produce an intermediate (prepolymer), followed by a second, polycondensation step. The first step may be catalyzed by an esterification/transesterification catalyst at a temperature from about 150° C. (302° F.) to about 250° C. (482° F.) and carried out until the concentration of the starting monomer(s) or ester derivative monomer(s) is reduced to less than about 3 mol-%. The catalyst may comprise an organotin(IV) compound, present in a concentration from about 0.01 mol-% to about 0.2 mol-% in a polymer forming reaction mixture, relative to the starting monomer(s) or ester derivative(s). The prepolymer, as described herein, may therefore be the reaction product of two diol monomers and one monomer bearing a furandicarboxylate moiety that is ultimately present in the backbone of the resulting polymer.

Other diols of interest for forming the intermediate (prepolymer) include those, like FDCA, which may be bio-derived, such as in the case of isohexides. These compounds are bicyclic, rigid diols that differ only in the orientation of the hydroxyl groups at $C_2$ and $C_5$ ring positions, and they can be obtained by cyclodehydration of hexitols. For example, isomannide can be obtained (endo-endo) from mannitol, isosorbide (exo-endo) can be obtained from sorbitol, and isoidide (exo-exo) can be obtained from iditol. Regardless of the particular diol, the intermediate (prepolymer) that is formed may optionally be isolated from the reaction mixture of the first reaction step, although generally this is not necessary. The second step of polycondensation may be catalyzed and performed under reduced pressure (e.g., 100 Pascal (Pa) or less), at a temperature in the range of the melting point of the resulting copolymer to about (54° F.) above this temperature, and preferably at a temperature of at least about 180° C. (356° F.). The polycondensation catalyst may comprise a tin(II) compound, such as tin(II) oxide or an organotin(II) compound. Otherwise, a catalyst based on titanium may be employed, such as titanium or a chelated titanium compound, having various ligands that can include alkoxides, for example propoxide or tert-butoxide. Representative catalysts are therefore titanium (IV) propoxide and titanium (IV) tert-butoxide.

FDCA or a derivative thereof may also be used in forming polymers other than polyester polymers. For example, polyamide polymers may be formed in the case of reacting FDCA or a derivative thereof with a co-monomer having at least two amino groups (e.g., a diamine), to produce a polyamide having FDCA-related moieties. Suitable co-monomers include aliphatic diamines such as hexamethylene diamine and aromatic diamines such as paraphenylene diamine. As also described above, a derivative of FDCA may be used in forming polyester polymers. For example, polyester polymers may be formed in the case of reacting, as a co-monomer, a hydroxyl (alcohol) derivative of FDCA (e.g., a diol derivative of FDCA), with a polyacid (e.g., FDCA) to produce a polyester having FDCA-related moieties. Suitable co-monomers that are hydroxyl derivatives of FDCA include furan 2,5-diol and furan 2,5-dimethanol.

FDCA or a derivative thereof may be used, for example, in forming polyurethane polymers, in the case of reacting, as a co-monomer, a hydroxyl (alcohol) derivative of FDCA (e.g., a diol derivative), with a polyisocyanate to produce a polyurethane having FDCA-related moieties. Suitable co-monomers that are hydroxyl derivatives of FDCA include those described above with respect to the formation of polyester polymers. Suitable polyisocyanates include diisocyanates, and in particular aromatic diisocyanates such as toluene diisocyanate, methylene diphenyl diisocyanate, and polymeric methylene diisocyanates. In other embodiments, polyamide polymers may be formed in the case of reacting, as a co-monomer, an amino derivative of FDCA (e.g., a diamino derivative), with a polyacid (e.g., FDCA) to produce a polyamide having FDCA-related moieties. Suitable co-monomers that are amino derivatives of FDCA include furan 2,5-diamine and furan 2,5-dialkyl amines such as furan 2,5-dimethanamine. In other embodiments, polyamide polymers may be formed in the case of reacting an acyl derivative of FDCA (e.g., a diacyl chloride derivative of FDCA), with a co-monomer having at least two amino groups (e.g., a diamine), to produce a polyamide having FDCA-related moieties. Suitable acyl derivatives of FDCA include furan 2,5-diformyl chloride and furan 2,5-dialkyl chlorides such as furan 2,5-diacetyl chloride. Suitable co-monomers include aliphatic diamines such as hexamethylene diamine and aromatic diamines such as paraphenylene diamine. In other embodiments, polyurethane polymers may be formed in the case of reacting an isocyanate derivative of FDCA (e.g., a diisocyanate derivative of FDCA), separately or in combination, with a co-monomer having at least two hydroxyl groups (e.g., a diol), to produce a polyurethane having FDCA-related moieties. Suitable isocyanate derivatives of FDCA include furan 2,5-diisocyanate and furan 2,5-dialkyl isocyanates such as furan 2,5-dimethanisocyanate. Suitable co-monomers include diols such as those described above for forming an intermediate (prepolymer) used to ultimately produce a polyester polymer. In still other embodiments polycarbonate polymers may be formed in the case of reacting a hydroxyl (alcohol) derivative of FDCA (e.g., a diol derivative of FDCA), with phosgene to produce a polycarbonate having FDCA-related moieties. Suitable hydroxyl derivatives of FDCA include those described above with respect to co-monomers the formation of polyester polymers.

As described above, benefits attained from modifying humins in an oxidative pretreatment, and particularly those benefits resulting from improved properties, such as reduced color and increased color stability, may advantageously extend to downstream products described herein, including monomer compositions comprising FDCA, compositions comprising esterified derivatives of FDCA (e.g., FDME), compositions comprising prepolymers (e.g., esterified and transesterified derivatives of FDCA), and bio-based copolymers.

The following examples are set forth as representative of the present invention. These examples are illustrative and not to be construed as limiting the scope of the invention as defined in the appended claims.

Examples

Effect of Oxidative Pretreatment with Oxidizing Agents, on the Color of Dehydration Products Experiments were performed to evaluate the effect of treating products, obtained from the dehydration of fructose using a dehydration feed with 10 wt-% dry solids, with various oxidizing agents. These oxidizing agents and the amounts used, expressed as both a molar percentage, as well as a molar oxidizing equivalent percentage, relative to FDCA-forming furanics in the dehydration product (or relative to fructose sugar in the dehydration feed), are summarized in Table 1 below.

TABLE 1

Oxidizing Agents and Molar Percentages

| Oxidant Screen | Loading (mol % relative to sugar) | Oxidizing Equivalents (mol % relative to sugar) |
|---|---|---|
| $MnO_2$ | 5/10 | 10/20 |
| NaOCl | 5/10 | 10/20 |
| $H_2O_2$ | 5/10 | 10/20 |
| oxone | 5/10 | 10/20 |
| percarbonate | 5/10 | 10/20 |
| MCPBA | 5/10 | 10/20 |
| peracetic | 5/10 | 10/20 |
| $KMnO_4$ | 5/10 | 25/50 |
| $NaIO_4$ | 5/10 | 35/70 |
| $KBrO_3$ | 4.4/8.8 | 35/70 |

In each case, the oxidizing agent was added in water to 1-2 ml of the dehydration product in a 20 ml scintillation vial and the contents were stirred for 2-3 hours at room temperature in the case of the 5 mol-% loading samples and stirred overnight at room temperature in the case of the 10 mol-% loading samples. Following the oxidations for these time periods, the samples were analyzed for humins and "on-path" furanics, or namely the FDCA-forming furanics HMF, 5-(acetoxymethyl)furfural, and HMF dimer. Based on these analyses, yields of humins, as well as yields of FDCA-forming furanics, were minimally impacted. Even for the 10 mol-% loading samples, approximately 80-95 wt-% of the starting quantity of humins was maintained, following the oxidations. For the 5 mol-% loading samples, these yields were higher. A control sample without oxidizing agent confirmed that the humin yield, according to analyses at time periods before and after the oxidations, was 100 wt-%. In addition, the yields of FDCA-forming furanics were nearly 100 mol-% in all cases, and the control sample was analyzed to confirm 100 mol-% yield also with respect to FDCA-forming furanics.

The absorption spectra for each of these samples over UV and visible wavelengths from 360 nanometers (nm) to 710 nm were evaluated, compared to the control sample, and indicated generally reduced absorption over these wavelengths, corresponding to generally lighter color. Specific measurements of absorption for the mol-% loading samples were made at 460 nm, and results showed that absorbance was decreased to a value of as low as about 42% of that of the control sample, representing an untreated dehydration product or starting composition. This largest decreased in absorbance was achieved with $KBrO_3$ as the oxidizing agent. Generally, however, absorbance values of 80% or less, and in some cases 60% or less, relative to the control sample were obtained. The change in absorbance at 460 nm, per mol-% of oxidizing equivalents, was also evaluated. On this basis, hydrogen peroxide ($H_2O_2$) and mCPBA (meta-chloroperoxybenzoic acid) were the most effective oxidants.

A Bromine Source as an Oxidizing Agent

Molecular bromine ($Br_2$), as a bromine source yielding $Br^-$ ions in aqueous solution, was also investigated for its effects on the color of a dehydration product as described above, i.e., obtained from the dehydration of fructose using a dehydration feed with 10 wt-% dry solids. Various amounts of this bromine source/oxidizing agent were added in water, in each case, to 1-2 ml of the dehydration product in a 20 ml scintillation vial and the contents were stirred overnight at room temperature. These various amounts corresponded to various molar oxidizing equivalent percentages, relative to FDCA-forming furanics in the dehydration product (or relative to fructose sugar in the dehydration feed). With up to 50 mol-% oxidizing equivalents, the humin yield was minimally impacted, as over 95 wt-% of the starting quantity of humins was maintained, following the oxidation. Also at this loading, the yield of FDCA-forming furanics exceeded 80 mol-% and the measured absorption of light having a wavelength of 460 nm, in the case of the pretreated dehydration product, was about 60% of that measured for the starting dehydration product. At a loading of about 90 mol-% oxidizing equivalents, the yields of humins and FDCA-forming furanics were reduced to about 95 wt-% and less than 60 mol-%, respectively. However, the measured absorption of light having a wavelength of 460 nm was about 30% of that measured for the starting dehydration product. Accordingly, it can be appreciated that sources of Br can be effective oxidizing/bleaching agents, insofar are they can significantly decrease the color of a pretreated dehydration product, while only moderately or negligibly impacting amounts of FDCA-forming furanics present in this product. Quantities of humins were also substantially retained. Without being bound by theory, it is believed that sources of Br in aqueous solution may become oxidized to Br 2 at some stage of the oxidative pretreatment/bleaching, and that this oxidized form can then contribute to the selective bleaching of humins.

Hydrogen Peroxide as an Oxidizing Agent, Optionally with Catalyst and/or Acid

The oxidizing agent hydrogen peroxide ($H_2O_2$) was specifically investigated for its effects, with and without the addition of the catalytic metals Co and/or Mn, and/or the addition of nitric acid ($HNO_3$), on the color of a dehydration product as described above, i.e., obtained from the dehydration of fructose using a dehydration feed with 10 wt-% dry solids. In the absence of any catalyst or acid, amounts of $H_2O_2$ representing mol-%, 15 mol-%, 20 mol-%, 30 mol-%, and 40 mol-%, relative to FDCA-forming furanics in the dehydration product (or relative to fructose sugar in the dehydration feed), were added in water, in each case, to 1-2 ml of the dehydration product in a 20 ml scintillation vial and the contents were maintained at room temperature for a period of 3 days. The preparation of these samples was repeated, and separate oxidative pretreatment steps were performed at 50° C. for a period of 4 hours. In both the room temperature and elevated temperature experiments, the pretreated dehydration products exhibited progressively lighter color, based on visual observation, with increasing $H_2O_2$ loadings. Also, at a loading of 30 mol-% $H_2O_2$, in both the room temperature and elevated temperature experiments, the yields of both humins and FDCA-forming furanics were favorable, being at or greater than 80 wt-% and 90 mol-%, respectively, relative to the dehydration products initially. Also at this loading, the measured absorption of light having a wavelength of 460 nm, for the pretreated dehydration products obtained following the room temperature and 50° C. oxidative pretreatments, was about 36% of that measured for the starting dehydration product in each case. At loadings of 40 mol-% $H_2O_2$, losses in the yields of FDCA-forming furanics became more pronounced.

In view of these results, a loading of 30 mol-% $H_2O_2$ was selected for further investigation of the effects of adding the catalytic metals Co and/or Mn, and/or adding nitric acid. Metals were added in their soluble acetate forms. Specifically, according to further experiments, amounts of $H_2O_2$ representing 30 mol-% relative to FDCA-forming furanics in the dehydration product (or relative to fructose sugar in the dehydration feed), were added in water, in each case, to 1-2 ml of the dehydration product in 20 ml scintillation vials. In addition to this loading of $H_2O_2$, also added to separate vials were (i) Co representing 2 mol-% relative to FDCA-forming furanics, (ii) Mn representing 2 mol-% relative to FDCA-forming furanics, (iii) Co and Mn each representing 2 mol-% relative to FDCA-forming furanics, (iv) $HNO_3$ representing 0.5 mol-% relative to FDCA-forming furanics (v) Co and $HNO_3$ representing 2 mol-% and mol-%, respectively, relative to FDCA-forming furanics, (vi) Mn and $HNO_3$ representing 2 mol-% and 0.5 mol-%, respectively, relative to FDCA-forming furanics, and (vii) Co and Mn each representing 2 mol-% relative to FDCA-forming furanics, and $HNO_3$ representing 0.5 mol-%, relative to FDCA-forming furanics. The contents of these vials were in each case maintained at room temperature with stirring overnight. Compared to a control vial containing the dehydration product that was maintained under the same conditions but without added $H_2O_2$, catalyst, or metals, the vials (i)-(vii) were all lighter in color, based on visual observation.

Further experiments investigated the effects of various loadings of $H_2O_2$ for its effects, in combination with Co representing 2 mol-% relative to FDCA-forming furanics, on the color of a dehydration product as described above, i.e., obtained from the dehydration of fructose using a dehydration feed with 10 wt-% dry solids. In each case, this oxidizing agent and catalyst were added in water to 1-2 ml of the dehydration product in 20 ml scintillation vials, and the contents were maintained at room temperature for a period of 3 days. The Co was added in its soluble acetate form. At a loading of 20 mol-% $H_2O_2$, the yields of both humins and FDCA-forming furanics were favorable, being at or greater than 80 wt-% and 95 mol-%, respectively, relative to the dehydration products initially. Also, at this loading, the measured absorption of light having a wavelength of 460 nm, for the pretreated dehydration products decreased to about 40% of that measured for the starting dehydration product. At a loading of 40 mol-% $H_2O_2$, yields of FDCA-forming furanics were still in excess of 95 mol-%, and the measured absorption of light having a wavelength of 460 nm, for the pretreated dehydration products, decreased to about 20% of that measured for the starting dehydration product.

Dehydration Products Obtained from Dehydration Feeds with Higher Dry Solids Content Additional experiments were performed to investigate the effect of hydrogen peroxide on the color of a dehydration product, in this case obtained from the dehydration of fructose using a dehydration feed with 20 wt-% dry solids. This higher dry solids content, relative to that investigated in other experiments, led to the use of greater amounts of $H_2O_2$, representing as much as 200 mol-% relative to FDCA-forming furanics in the dehydration product (or relative to fructose sugar in the dehydration feed). In each case, this oxidizing agent was added in water to 1-2 ml of the dehydration product in 20 ml scintillation vials, and the contents were maintained at room temperature for a period of 3 days. At loadings approaching 50 mol-% $H_2O_2$, the yields of both humins and FDCA-forming furanics were favorable, being at or greater than 95 wt-% and 85 mol-%, respectively, relative to the dehydration products initially. Also, at these loadings, the measured absorption of light having a wavelength of 460 nm, for the pretreated dehydration products, decreased to about 60% of that measured for the starting dehydration product. At loadings of 80-100 mol-% $H_2O_2$, losses in the yields of FDCA-forming furanics became more pronounced.

Further experiments investigated the effects of various loadings of $H_2O_2$ for its effects, in combination with Co representing 20 mol-% relative to FDCA-forming furanics, on the color of a dehydration product obtained from a feed having a higher content of dry solids as described above, i.e., obtained from the dehydration of fructose using a dehydration feed with 20 wt-% dry solids. Again, this higher dry solids content, relative to that investigated in other experiments, led to the use of greater amounts of $H_2O_2$, representing as much as 200 mol-% relative to 1-DCA-forming furanics in the dehydration product (or relative to fructose sugar in the dehydration feed). In each case, this oxidizing agent and catalyst were added in water to 1-2 ml of the dehydration product in 20 ml scintillation vials, and the contents were maintained at room temperature for a period of 3 days. The Co was added in its soluble acetate form. At a loading approaching 50 mol-% $H_2O_2$, the yields of both humins and FDCA-forming furanics were favorable, being at or greater than 80 wt-% and 95 mol-%, respectively, relative to the dehydration products initially. Also, at this loading, the measured absorption of light having a wavelength of 460 nm, for the pretreated dehydration products, decreased to about 32% of that measured for the starting dehydration product. At a loading of 100 mol-% $H_2O_2$, yields of FDCA-forming furanics were nearly 90 mol-%, and the measured absorption of light having a wavelength of 460 nm, for the pretreated dehydration products, decreased to about 18% of that measured for the starting dehydration product. In the case of dehydration products obtained from the dehydration of fructose using a dehydration feed with 20 wt-% dry solids, oxidative pretreatment was found to have an effect of decreasing humin molecular weight, whereas this effect was not observed in experiments using dehydration products obtained from dehydration feeds with 10 wt-% dry solids.

Effect of Oxidative Pretreatment on the Subsequent Oxidation of FDCA-Forming Furanics An experiment was performed to evaluate the effect of oxidative pretreatment on the subsequent oxidation of FDCA-forming furanics, namely the "on path" furanics of HMF, 5-(acetoxymethyl)furfural, and HMF dimer, representative of products obtained from the dehydration of fructose in the presence of an acetic acid and water solvent system. The untreated (baseline) dehydration product and the pretreated dehydration product, used in comparative experiments, each contained 8.5 wt-% of these compounds, in solution with this solvent system. An oxidation reactor used for the experiments was charged in each case with a homogeneous catalyst composition comprising cobalt, manganese, and bromine at concentrations of 1000 wt-ppm, 932 wt-ppm, and 1926 wt-ppm, respectively. Oxidation reaction conditions included a temperature of 180° C. and a total pressure of 15.2 bar (220 psi), with feed rates of the dehydration product and air to the oxidation reactor being maintained at 0.9 milliliters per minute (ml/min) and 550 standard cubic centimeters per minute (sccm), respectively, for a target reaction time of 150 minutes. This target reaction time was namely a maximum time over which the reaction in each experiment was performed, with the possibility for shorter reaction times to result in cases of loss of "light off," as indicated by a drop in oxygen consumption. Following each reaction, the contents of the oxidation reactor were analyzed to determine the amounts of FDCA present, as well as amounts of FDCA-forming intermediates, such as 5-hydroxymethyl-2-furancarboxylic acid and 5-formyl-2-furancarboxylic acid, which were nonetheless valuable reaction products in terms of their ability to undergo further oxidation to form 1-DCA.

Importantly, the baseline experiment was conducted for only approximately 120 minutes, at which time the reaction light off was lost and no further conversion ensued. In contrast, using the pretreated dehydration product, the reaction could be maintained until almost the entire target reaction time of 150 minutes. Accordingly, the use of this product advantageously resulted in a stabilizing effect on the oxidation of FDCA-forming furanics to FDCA.

Results from the Investigation of Oxidizing Agents/Conditions

In view of these results, based on the retention of humins before and after oxidation, the color characteristics of these contaminants appeared to have been modified (by humin "bleaching") due to the presence of the chemical oxidants studied, even in sub-stoichiometric amounts. Oxidation conditions could be adjusted to achieve selective oxidation of humin functional groups over FDCA-forming furanics, with minimal impacts in many cases to humin content. Also, the use of catalysts, such as soluble Co and/or Mn, could increase oxidation (bleaching) rates as well as oxidation selectivity to humin functional groups, for a given system. Increasing temperature could also be used to accelerate oxidation. Furthermore, significantly higher loadings of oxidizing agent were needed to effectively oxidize higher molecular weight humins, present in higher amounts, in dehydration products obtained from feeds having higher dry solids contents. In addition, an oxidative pretreatment step utilizing a 1 mol-% Co—Mn—$HNO_3$ catalyst system and 30 mol-% $H_2O_2$, with molar percentages being relative to FDCA-forming furanics, was selected for scale-up and treating of 500 grams of a dehydration product obtained from the dehydration of fructose using a dehydration feed with 10 wt-% dry solids. Efficacy of this catalyst system was thereby shown on the pilot/demonstration scale.

With knowledge gained from the present disclosure, those skilled in the art can effectively tailor conditions and catalysts, in using a broad scope of oxidizing agents, to achieve selective oxidation/bleaching of humins, thereby gaining advantages taught herein, such as improved stability in oxidizing FDCA-forming furanics to FDCA and realizing other beneficial effects. It will also be recognized that various changes can be made to the oxidative pretreatment processing steps, oxidizing agents, catalysts, and conditions in attaining these and other advantages, without departing from the scope of the present disclosure.

What is claimed is:

1. A process for pretreating a dehydration product of one or more carbohydrates having a 6-carbon sugar unit, the process comprising:

in an oxidative pretreatment step, contacting the dehydration product with an oxidizing agent to provide a pretreated dehydration product having an improved property resulting from modifying humins present in the dehydration product, wherein the oxidative pretreatment step is characterized by a selective modification of humins without substantial conversion of 2,5-furandicarboxylic acid- (FDCA-) forming furanics, and the FDCA-forming furanics in the pretreated dehydration product represent at least about 80 mol-% of those present in the dehydration product, prior to oxidative pretreatment.

2. The process of claim 1, wherein the improved property is a reduction in an absorption of ultraviolet or visible radiation, a reduction in color of downstream products, a decrease in average molecular weight of humins, an increase in a quantity of precipitated humins, or an increase in stability as an oxidation feed for producing FDCA.

3. The process of claim 2, wherein the improved property is the reduction in the absorption of light having a wavelength of 460 nanometers (nm).

4. The process of claim 3, wherein the absorption of light having a wavelength of 460 nm is about 60% or less, relative to that of the dehydration product.

5. The process of claim 1, wherein the oxidizing agent is a transition metal oxide, an alkali or alkaline earth metal oxyhalide, an alkali or alkaline earth metal percarbonate, an alkali or alkaline earth metal permanganate, an alkali or alkaline earth metal chlorate or perchlorate, an alkali or alkaline earth metal bromate or perbromate, an alkali or alkaline earth metal iodate or periodate, an alkali or alkaline earth metal sulfate or persulfate, a peroxide, a peroxy acid, or oxygen.

6. The process of claim 5, wherein the oxidizing agent is selected from the group consisting of $MnO_2$, NaOCl, $H_2O_2$, $KHSO_5$, $Na_2CO_3 \cdot 1.5H_2O_2$, meta-chloroperoxybenzoic acid, peracetic acid, $KMnO_4$, $NaIO_4$, $KBrO_3$, and combination thereof.

7. The process of claim 1, wherein the oxidizing agent is a bromine source.

8. The process of claim 1, wherein, in the oxidative pretreatment step, the oxidizing agent is present, or is added, in an amount representing from about 5 mol-% to about 70 mol-% of oxidizing equivalents, relative to FDCA-forming furanics in the dehydration product.

9. The process of claim 1, wherein, in the oxidative pretreatment step, an average residence time is at least 1 hour.

10. The process of claim 1, wherein, in the oxidative pretreatment step, an average temperature is from about 20° C. to about 120° C.

11. The process of claim 1, wherein, in the oxidative pretreatment step, the dehydration product and the oxidizing agent are contacted in the presence of a catalyst, wherein the catalyst comprises Co, Mn, and/or an acid.

12. The process of claim 11, wherein the Co and/or Mn are independently present in an amount, or present in a combined amount, representing from about 0.1 mol-% to about 10 mol-% of FDCA-forming furanics in the dehydration product.

13. The process of claim 11, wherein the acid is present in an amount representing from about 0.05 mol-% to about 5 mol-% of FDCA-forming furanics in the dehydration product.

14. A process for making a monomer composition comprising 2,5-furan dicarboxylic acid (FDCA), the process comprising:

in an oxidative pretreatment step, contacting a dehydration product of one or more carbohydrates having a 6-carbon sugar unit with an oxidizing agent to provide a pretreated dehydration product, wherein the oxidative pretreatment step is characterized by a selective modification of humins without substantial conversion of FDCA-forming furanics, and the FDCA-forming furanics in the pretreated dehydration product represent at least about 80 mol-% of those present in the dehydration product, prior to oxidative pretreatment, in an oxidation step, contacting the pretreated dehydration product in the presence of oxygen, with an oxidation catalyst to provide the composition comprising FDCA, wherein, in the oxidation step, a yield of FDCA, based on FDCA-forming furanics in the pretreated dehydration product, is at least about 60 mol-%.

15. The process of claim 14, wherein an oxidative pretreatment temperature used in the oxidative pretreatment step is lower than an oxidation temperature used in the oxidation step.

16. The process of claim 15, wherein the oxidative pretreatment temperature is from about 20° C. to about 120° C.

17. A process for making a monomer composition comprising 2,5-furan dicarboxylic acid (FDCA), the process comprising:

in an oxidative pretreatment step, contacting a dehydration product of one or more carbohydrates having a 6-carbon sugar unit with an oxidizing agent to provide a pretreated dehydration product, wherein the oxidative pretreatment step is characterized by a selective modification of humins without substantial conversion of FDCA-forming furanics, and the FDCA-forming furanics in the pretreated dehydration product represent at least about 80 mol-% of those present in the dehydration product, prior to oxidative pretreatment, in an oxidation step, contacting the pretreated dehydration product in the presence of oxygen, with an oxidation catalyst to provide the composition comprising FDCA, wherein an amount of the oxidizing agent that is added, or that is present, relative to FDCA-forming furanics in the dehydration product, is adjusted based on (i) a dry solids content of a dehydration feed that is subjected to a dehydrating step to obtain the dehydration product or (ii) a humin content of the dehydration product.

18. The process of claim 17, wherein the dry solids content of the dehydration feed is from about 5 wt-% to about 35 wt-%.

* * * * *